(12) United States Patent
Ootake et al.

(10) Patent No.: US 7,524,917 B2
(45) Date of Patent: Apr. 28, 2009

(54) ORGANOSILICON COMPOUND AND PRODUCTION PROCESS FOR THE SAME, AND POLYSILOXANE AND PRODUCTION PROCESS FOR THE SAME

(75) Inventors: Nobumasa Ootake, Ichihara (JP); Kazuhiro Yoshida, Ichihara (JP)

(73) Assignees: Chisso Petrochemical Corporation, Tokyo (JP); Chisso Corporation, Osaka (JP)

( * ) Notice: Subject to any disclaimer, the term of this patent is extended or adjusted under 35 U.S.C. 154(b) by 73 days.

(21) Appl. No.: 10/562,817

(22) PCT Filed: Jun. 30, 2004

(86) PCT No.: PCT/JP2004/009618

§ 371 (c)(1),
(2), (4) Date: Jan. 25, 2006

(87) PCT Pub. No.: WO2005/000857

PCT Pub. Date: Jan. 6, 2005

(65) Prior Publication Data

US 2006/0155091 A1    Jul. 13, 2006

(30) Foreign Application Priority Data

Jun. 30, 2003  (JP) ............... 2003-186904
Apr. 28, 2004  (JP) ............... 2004-133045

(51) Int. Cl.
    *C08G 77/16*    (2006.01)
(52) U.S. Cl. .......................... 528/33; 528/37
(58) Field of Classification Search ........ None
    See application file for complete search history.

(56) References Cited

U.S. PATENT DOCUMENTS 6,927,270 B2 * 8/2005 Lichtenhan et al. ........... 528/12
7,169,873 B2 * 1/2007 Morimoto et al. ............. 528/37
2003/0055193 A1 * 3/2003 Lichtenhan et al. ........... 528/10

FOREIGN PATENT DOCUMENTS

EP        1 428 795     6/2004
WO        03/024870     3/2003

* cited by examiner

*Primary Examiner*—Marc S Zimmer
(74) *Attorney, Agent, or Firm*—Wenderoth, Lind & Ponack, L.L.P.

(57) ABSTRACT

The present invention provides a novel organosilicon compound and polysiloxane which are useful as electronic materials, optical materials, coating materials, sealing materials and catalyst carriers and which can be used as additives for improving various physical properties such as flame retardancy, heat resistance, weatherability, light resistance, electric insulating property, a surface characteristic, hardness, a mechanical strength and a chemical resistance of a polymer material. That is, the present invention relates to an organosilicon compound represented by Formula (1) and polysiloxane comprising the above organosilicon compound as a monomer:

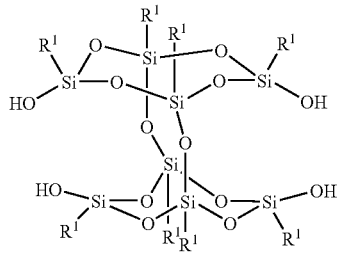

(1)

11 Claims, No Drawings

ORGANOSILICON COMPOUND AND PRODUCTION PROCESS FOR THE SAME, AND POLYSILOXANE AND PRODUCTION PROCESS FOR THE SAME

FIELD OF THE INVENTION

The present invention relates to an organosilicon compound and a production process for the same and to polysiloxane and a production process for the same.

BACKGROUND ART

A lot of researches on silsesquioxane have so far been made, and a large number of reports are present. For example, according to a general remark (non-patent document 1) issued by Baney et al., it is confirmed that an amorphous structure which does not show a fixed structure in addition to a ladder structure, a cage structure and an incompletely condensed structure is present in silsesquioxane. In the present specification, an incompletely condensed structure means a structure in which at least one part of a cage structure is not closed.

Among organosilicon compounds having silanol, the following compounds can be given as publicly known compounds.

Among compounds represented by Formula (4), the compound in which a substituent represented by $R^4$ is cyclohexyl is reported by Brown et al. (non-patent document 2); the compounds in which it is cyclopentyl and cycloheptyl are reported by Feher et al. (non-patent document 3); and the compounds in which it is methyl, ethyl, isobutyl and cyclohexyl are reported by Lichtenhan et al. (patent document 1).

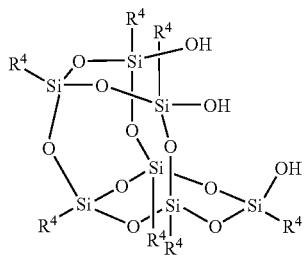

(4)

In recent years, the silsesquioxanes represented by Formula (4) having an incompletely condensed structure are commercially available from Hybrid Plastics Inc. of U.S.A., but the kinds thereof are limited.

Among cyclic compounds represented by Formula (5), the compound in which a substituent represented by $R^5$ is cyclohexyl or phenyl is reported by Brown et al. (non-patent document 2 or non-patent document 4), and the compound in which it is isopropyl is reported by Unno et al. (non-patent document 5).

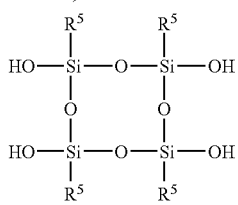

(5)

Further, an organosilicon compound of a ladder structure represented by Formula (6) having silanol at an end is reported by Unno et al. (non-patent document 6).

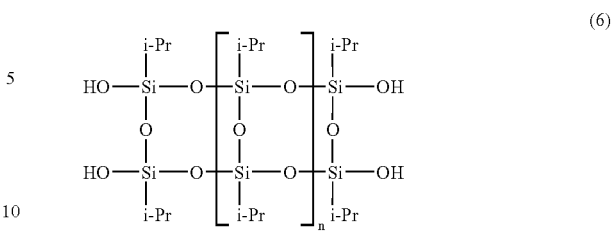

(6)

In Formula (6), i-Pr represents isopropyl, and n is an integer of 1 to 4.

However, it has not been known that present is an organosilicon compound of a double decker structure represented by Formula (1) which has silanol and which is provided by the present invention. Accordingly, polysiloxane obtained by using the above organosilicon compound has not been known as well.

Non-patent document 1: Chem. Rev. 95, 1409 (1995)
Non-patent document 2: J. Am. Chem. Soc., 87, 4313 (1965)
Non-patent document 3: Organometallics, 10, 2526 (1991)
Non-patent document 4: J. Am. Chem. Soc., 87, 4317 (1965)
Non-patent document 5: Chem. Lett., 489 (1998)
Non-patent document 6: J. Am. Chem. Soc., 124, 1574 (2002)
Non-patent document 7: Organometallics, 19, 1077 (2000)
Patent document 1: WO 01/10871
Patent document 2: JP H1-98631 A/1989
Patent document 3: JP H1-272633 A/1989

DISCLOSURE OF THE INVENTION

Because of physical properties originating in a structure thereof, silsesquioxane is expected to be applied to wide uses such as, for example, electronic materials, optical materials, coating materials, sealing materials and catalyst carriers. However, the kind of silsesquioxanes which are actually commercially available and have high practicality is very small.

As described above, a large number of reports on silsesquioxane is present, but an organosilicon compound of a double decker structure having silanol represented by Formula (1) has not so far been known.

In light of such problems of conventional techniques as described above, the present inventors have intensively repeated researches. As a result thereof, they have found that an organosilicon compound having silanol represented by Formula (1) can readily be obtained at a good yield by reacting an organosilicon compound represented by Formula (2) with a proton donor. Further, they have found that useful polysiloxane is obtained by reacting the organosilicon compound having silanol represented by Formula (1) with an organosilicon compound having a hydrolytic group or silanol, and thus they have completed the present invention.

The organosilicon compound and the polysiloxane according to the present invention are useful as electronic materials, optical materials, coating materials, sealing materials and catalyst carriers. Further, the organosilicon compound and the polysiloxane according to the present invention can also be used as additives for improving various physical properties such as flame retardancy, heat resistance, weatherability, light resistance, electric insulating property, a surface characteristic, hardness, a mechanical strength and a chemical resistance of a polymer material.

The present invention comprises the following structures.

[1] An organosilicon compound represented by Formula (1):

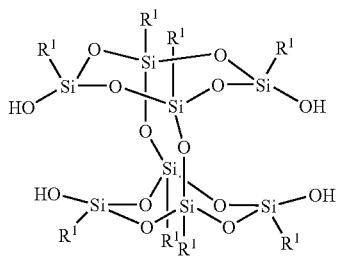

(1)

wherein each $R^1$ is group selected independently from hydrogen, alkyl having 1 to 45 carbon atoms in which optional hydrogen may be replaced by fluorine and in which optional —$CH_2$— may be replaced by —O—, —CH=CH—, cycloalkylene or cycloalkenylene, substituted or unsubstituted aryl and arylalkyl constituted of alkylene in which optional hydrogen may be replaced by fluorine and optional —$CH_2$— may be replaced by —O—, —CH=CH— or cycloalkylene and substituted or unsubstituted aryl.

[2] The organosilicon compound as described in the above item [1], wherein each $R^1$ is group selected independently from hydrogen and alkyl having 1 to 30 carbon atoms in which optional hydrogen may be replaced by fluorine and optional —$CH_2$— may be replaced by —O— or cycloalkylene.

[3] The organosilicon compound as described in the above item [1], wherein each $R^1$ is group selected independently from hydrogen, alkenyl having 2 to 20 carbon atoms in which optional hydrogen may be replaced by fluorine and optional —$CH_2$— may be replaced by —O— or cycloalkylene and alkyl having 1 to 20 carbon atoms in which optional hydrogen may be replaced by fluorine and at least one —$CH_2$— is replaced by cycloalkenylene.

[4] The organosilicon compound as described in the above item [1], wherein each $R^1$ is group selected independently from hydrogen, phenyl in which optional hydrogen may be replaced by halogen or alkyl having 1 to 10 carbon atoms and naphthyl; in which in the alkyl which is a substituent of the phenyl optional hydrogen may be replaced by fluorine and optional —$CH_2$— may be replaced by —O—, —CH=CH—, cycloalkylene or phenylene; and when the phenyl or the naphthyl has plural substituents, the substituents may be the same group or different groups.

[5] The organosilicon compound as described in the above item [1], wherein each $R^1$ is group selected independently from hydrogen and phenylalkyl constituted of phenyl in which optional hydrogen may be replaced by halogen or alkyl having 1 to 10 carbon atoms and alkylene having 1 to 12 carbon atoms; in which in the alkyl which is a substituent of the phenyl optional hydrogen may be replaced by fluorine and optional —$CH_2$— may be replaced by —O—, —CH=CH—, cycloalkylene or phenylene, in the above alkylene optional hydrogen may be replaced by fluorine and optional —$CH_2$— may be replaced by —O— or cycloalkylene; and when the phenyl has plural substituents, the substituents may be the same group or different groups.

[6] The organosilicon compound as described in the above item [1], wherein each $R^1$ is group selected independently from hydrogen and phenylalkenyl constituted of phenyl in which optional hydrogen may be replaced by halogen or alkyl having 1 to 10 carbon atoms and alkenylene having 2 to 12 carbon atoms; in which in the alkyl having 1 to 10 carbon atoms which is a substituent of the phenyl optional hydrogen may be replaced by fluorine and optional —$CH_2$— may be replaced by —O—, —CH=CH—, cycloalkylene or phenylene, in the above alkenylene optional hydrogen may be replaced by fluorine and optional —$CH_2$— may be replaced by —O— or cycloalkylene; and when the phenyl has plural substituents, the substituents may be the same group or different groups.

[7] The organosilicon compound as described in the above item [1], wherein each $R^1$ is group selected independently from hydrogen, alkyl having 1 to 8 carbon atoms in which optional hydrogen may be replaced by fluorine and optional —$CH_2$— may be replaced by —O—, —CH=CH—, cycloalkylene or cycloalkenylene, phenyl in which optional hydrogen may be replaced by halogen, methyl or methoxy, phenylalkyl constituted of phenyl in which optional hydrogen may be replaced by fluorine, alkyl having 1 to 4 carbon atoms, vinyl or methoxy and alkylene having 1 to 8 carbon atoms in which optional —$CH_2$— may be replaced by —O—, —CH=CH— or cycloalkylene, and naphthyl; and when the phenyl has plural substituents, the substituents may be the same group or different groups.

[8] The organosilicon compound as described in the above item [1], wherein all $R^1$ are the same group selected from hydrogen, alkyl having 1 to 8 carbon atoms in which optional hydrogen may be replaced by fluorine and optional —$CH_2$— may be replaced by —O—, —CH=CH—, cycloalkylene or cycloalkenylene, phenyl in which optional hydrogen may be replaced by halogen, methyl or methoxy, phenylalkyl constituted of phenyl in which optional hydrogen may be replaced by fluorine, alkyl having 1 to 4 carbon atoms, vinyl or methoxy and alkylene having 1 to 8 carbon atoms in which optional —$CH_2$— may be replaced by —O—, —CH=CH— or cycloalkylene, and naphthyl; and when the phenyl has plural substituents, the substituents may be the same group or different groups.

[9] The organosilicon compound as described in the above item [1], wherein all $R^1$ are the same group selected from hydrogen, phenyl in which optional hydrogen may be replaced by halogen, methyl or methoxy, phenylalkyl constituted of phenyl in which optional hydrogen may be replaced by fluorine, alkyl having 1 to 4 carbon atoms, vinyl or methoxy and alkylene having 1 to 8 carbon atoms in which optional —$CH_2$— may be replaced by —O—, —CH=CH— or cycloalkylene, and naphthyl; and when the phenyl has plural substituents, the substituents may be the same group or different groups.

[10] The organosilicon compound as described in the above item [1], wherein all $R^1$ are phenyl.

[11] A production process for the organosilicon compound as described in the above item [1], characterized by using an organosilicon compound represented by Formula (2):

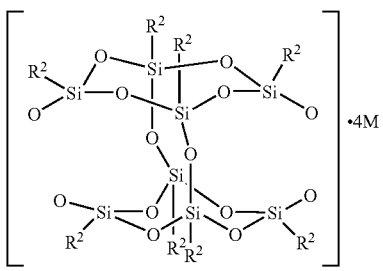

(2)

wherein $R^2$ has the same meaning as that of $R^1$ in Formula (1) described in the above item [1], and M is a monovalent alkaline metal atom.

[12] A production process for the organosilicon compound as described in the above item [1], characterized by reacting the organosilicon compound represented by Formula (2) with a proton donor.

[13] A production process for the organosilicon compound as described in the above item [1], characterized by reacting the organosilicon compound represented by Formula (2) with an inorganic acid.

[14] A production process for the organosilicon compound as described in the above item [1], characterized by reacting the organosilicon compound represented by Formula (2) with an organic acid.

[15] Polysiloxane represented by Formula (3):

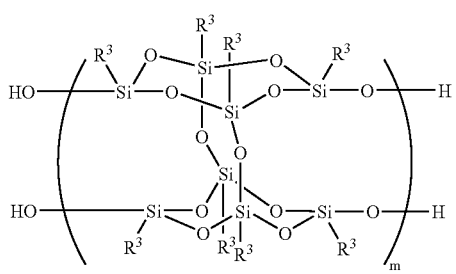

(3)

wherein $R^3$ has the same meaning as that of $R^1$ in Formula (1) described in the above item [1], and m is an integer of 2 to 1000.

[16] The polysiloxane as described in the above item [15], wherein m is an integer of 2 to 500.

[17] The polysiloxane as described in the above item [15], wherein m is an integer of 2 to 50.

[18] Polysiloxane obtained by subjecting the organosilicon compound as described in any of the above items [1] to [10] to polycondensation reaction.

[19] Polysiloxane obtained by reacting the organosilicon compound as described in any of the above items [1] to [10] with an organosilicon compound having a hydrolytic group.

[20] Polysiloxane obtained by reacting the organosilicon compound as described in any of the above items [1] to [10] with an organosilicon compound having silanol.

[21] The polysiloxane as described in the above item [19], wherein the hydrolytic group is an alkoxysilyl group.

[22] The polysiloxane as described in the above item [19], wherein the hydrolytic group is an acetoxysilyl group.

[23] The polysiloxane as described in the above item [19], wherein the hydrolytic group is a halosilyl group.

[24] The polysiloxane as described in the above item [19], wherein the hydrolytic group is an aminosilyl group.

[25] A production process for polysiloxane, characterized by subjecting the organosilicon compound as described in any of the above items [1] to [10] to polycondensation reaction.

[26] A production process for polysiloxane, characterized by reacting the organosilicon compound as described in any of the above items [1] to [10] with an organosilicon compound having a hydrolytic group.

[27] A production process for polysiloxane, characterized by reacting the organosilicon compound as described in any of the above items [1] to [10] with an organosilicon compound having silanol.

[28] The production process for polysiloxane as described in the above item [26], wherein the hydrolytic group is an alkoxysilyl group.

[29] The production process for polysiloxane as described in the above item [26], wherein the hydrolytic group is an acetoxysilyl group.

[30] The production process for polysiloxane as described in the above item [26], wherein the hydrolytic group is a halosilyl group.

[31] The production process for polysiloxane as described in the above item [26], wherein the hydrolytic group is an aminosilyl group.

In the present specification, silsesquioxane shall be used as a general term for compounds obtained by hydrolyzing and condensing trifunctional hydrolytic silicon compounds.

The organosilicon compound and the polysiloxane according to the present invention are novel compounds and expected to be used as electronic materials, optical materials, coating materials, sealing materials and catalyst carriers. Also, the organosilicon compound and the polysiloxane according to the present invention are expected as well to be used as additives for improving various physical properties such as flame retardancy, heat resistance, weatherability, light resistance, electric insulating property, a surface characteristic, hardness, a mechanical strength and a chemical resistance of a polymer material. Further, the polysiloxane comprising the organosilicon compound of the present invention as a monomer is expected to have a high compatibility with resins.

The production process for an organosilicon compound provided by the present invention makes it possible to readily obtain the organosilicon compound of the present invention at a good yield. Further, the production process for polysiloxane provided by the present invention makes it possible to readily obtain the useful polysiloxane of the present invention.

BEST MODE FOR CARRYING OUT THE INVENTION

In the following explanations, the organosilicon compound represented by Formula (1) shall be shown as the compound (1), and the organosilicon compound represented by Formula (2) shall be shown as the compound (2). Compounds represented by the other formulas shall be shown in the same manner.

Alkyls and alkylenes described in the present invention may be linear groups or branched groups in all cases. This shall apply to a case where optional hydrogen is replaced by halogen or a cyclic group in the above groups and a case where optional —CH$_2$— is replaced by —O—, —CH=CH—, cycloalkylene or cycloalkenylene.

The term "optional" used in the present invention show that not only the positions but also the numbers are optional. When plural hydrogens or —CH$_2$— are substituted, they each may be replaced by different groups. For example, when two —CH$_2$— are replaced by —O— and —CH=CH— in alkyl, alkoxyalkenyl or alkenyloxyalkyl are shown. In this case, all groups of alkoxy and alkenylene in the alkoxyalkenyl and alkenyl and alkylene in the alkenyloxyalkyl may be linear groups or branched groups. In the present invention, however, when it is described that optional —CH$_2$— is replaced by —O—, adjacent plural —CH$_2$— are not replaced by —O—.

The organosilicon compound provided by the present invention is represented by the following Formula (1):

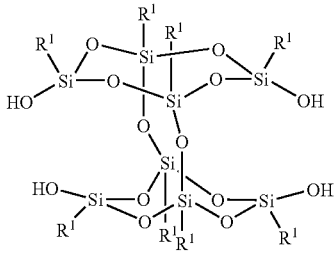

(1)

In Formula (1), each R$^1$ is group independently selected from the group consisting of hydrogen, alkyl having 1 to 45 carbon atoms, substituted or unsubstituted aryl and substituted or unsubstituted arylalkyl. All R$^1$ are preferably the same group but eight R$^1$ may be constituted of two or more different groups.

The combinations of a case where eight R$^1$ are constituted of different groups are, for example, a case where they are constituted of two or more alkyls, a case where they are constituted of two or more aryls, a case where they are constituted of two or more aralkyls, a case where they are constituted of hydrogen and at least one aryl, a case where they are constituted of at least one alkyl and at least one aryl, a case where they are constituted of at least one alkyl and at least one aralkyl and a case where they are constituted of at least one aryl and at least one aralkyl. They may be combinations other than the above examples. A process for producing the compound (1) having at least two different R$^1$ shall be described later.

When R$^1$ is alkyl, the number of carbon atoms is 1 to 45. The preferred carbon number is 1 to 30. More preferred carbon number is 1 to 8. Optional hydrogen thereof may be replaced by fluorine, and optional —CH$_2$— thereof may be replaced by —O—, —CH=CH—, cycloalkylene or cycloalkenylene. The preferred examples of the alkyl are non-substituted alkyl having 1 to 30 carbon atoms, alkoxyalkyl having 2 to 29 carbon atoms, a group in which one —CH$_2$— in alkyl having 1 to 8 carbon atoms is replaced by cycloalkylene, alkenyl having 2 to 20 carbon atoms, alkenyloxyalkyl having 2 to 20 carbon atoms, alkyloxyalkenyl having 2 to 20 carbon atoms, a group in which one —CH$_2$— in alkyl having 1 to 8 carbon atoms is replaced by cycloalkenylene, and groups in which optional hydrogens in the respective groups given above are replaced by fluorine. Cycloalkylene and cycloalkenylene having 3 to 8 carbon atoms is preferred.

The examples of unsubstituted alkyl having 1 to 30 carbon atoms are methyl, ethyl, propyl, 1-methylethyl, butyl, 2-methylpropyl, 1,1-dimethylethyl, pentyl, hexyl, 1,1,2-trimethylpropyl, heptyl, octyl, 2,4,4-trimethylpentyl, nonyl, decyl, undecyl, dodecyl, tetradecyl, hexadecyl, octadecyl, eicosyl, docosyl and triacontyl.

The examples of fluorinated alkyl having 1 to 30 carbon atoms are 3,3,3-trifluoropropyl, 3,3,4,4,5,5,6,6,6-nonafluorohexyl, tridecafluoro-1,1,2,2-tetrahydrooctyl, heptadecafluoro-1,1,2,2-tetrahydrodecyl, perfluoro-1,1,2,2-dodecyl and perfluoro-1,1,2,2-tetradecyl.

The examples of alkoxyalkyl having 2 to 29 carbon atoms are 3-methoxypropyl, methoxyethoxyundecyl and 3-heptafluoroisopropoxypropyl.

The examples of a group in which one —CH$_2$— in alkyl having 1 to 8 carbon atoms is replaced by cycloalkylene are cyclohexylmethyl, adamantaneethyl, cyclopentyl, cyclohexyl, 2-bicycloheptyl and cyclooctyl. Cyclohexyl is an example in which —CH$_2$— in methyl is replaced by cyclohexylene.

Cyclohexylmethyl is an example in which —CH$_2$— in ethyl is replaced by cyclohexylene.

The examples of alkenyl having 2 to 20 carbon atoms are ethenyl, 2-propenyl, 3-butenyl, 5-hexenyl, 7-octenyl, 10-undecenyl and 21-docosenyl. The example of alkenyloxyalkyl having 2 to 20 carbon atoms is allyloxyundecyl. The examples of alkyl which has 1 to 8 carbon atoms and in which one —CH$_2$— is replaced by cycloalkenylene are 2-(3-cyclohexenyl)ethyl, 5-(bicycloheptenyl)ethyl, 2-cyclopentenyl, 3-cyclohexenyl, 5-norbornene-2-yl and 4-cyclooctenyl.

The examples of a case where R$^1$ in Formula (1) is substituted or unsubstituted aryl are phenyl in which optional hydrogen may be replaced by halogen or alkyl having 1 to 10 carbon atoms and naphthyl. The preferred examples of halogen are fluorine, chlorine and bromine. In the alkyl having 1 to 10 carbon atoms, optional hydrogen may be replaced by fluorine, and optional —CH$_2$— may be replaced by —O—, —CH=CH— or phenylene.

That is, the preferred examples of a case where R$^1$ is substituted or unsubstituted aryl are phenyl, naphthyl, alkylphenyl, alkyloxyphenyl, alkenylphenyl, phenyl having as a substituent, alkyl having 1 to 10 carbon atoms in which optional —CH$_2$— is replaced by phenylene and groups in which optional hydrogens are replaced by halogens in the respective groups listed above. In the present invention, when called merely phenyl, it means unsubstituted phenyl unless otherwise described. The same shall apply to naphthyl.

The examples of halogenated phenyl are pentafluorophenyl, 4-chlorophenyl and 4-bromophenyl. The examples of alkylphenyl are 4-methylphenyl, 4-ethylphenyl, 4-propylphenyl, 4-butylphenyl, 4-pentylphenyl, 4-heptylphenyl, 4-octylphenyl, 4-nonylphenyl, 4-decylphenyl, 2,4-dimethylphenyl, 2,4,6-trimethylphenyl, 2,4,6- triethylphenyl, 4-(1-methylethyl)phenyl, 4-(1,1-dimethylethyl)phenyl, 4-(2-ethylhexyl)phenyl and 2,4, 6-tris (1-methylethyl) phenyl. The examples of alkyloxyphenyl are 4-methoxyphenyl, 4-ethoxyphenyl, 4-propoxyphenyl, 4-butoxyphenyl, 4-pentyloxyphenyl, 4-heptyloxyphenyl, 4-decyloxyphenyl, 4-octadecyloxyphenyl, 4-(1-methylethoxy)phenyl, 4-(2-methylpropoxy)phenyl and 4-(1,1-dimethylethoxy)phenyl. The examples of alkenylphenyl are 4-ethenylphenyl, 4-(1-methylethenyl)phenyl and 4-(3-butenyl)phenyl.

The examples of phenyl having as a substituent, alkyl having 1 to 10 carbon atoms in which optional —CH$_2$— is replaced by phenylene are 4-(2-phenylethenyl)phenyl, 4-phenoxyphenyl, 3-phenylmethylphenyl, biphenyl and terphenyl. 4-(2-Phenylethenyl)phenyl is an example in which one —CH$_2$— in ethyl of ethylphenyl is replaced by phenylene and in which the other —CH$_2$— is replaced by —CH=CH—.

The examples of phenyl in which a part of hydrogens on a benzene ring is replaced by halogen and in which other hydrogens are replaced by alkyl, alkyloxy or alkenyl are 3-chloro-4-methylphenyl, 2,5-dichloro-4-methylphenyl, 3,5-dichloro-4-methylphenyl, 2,3,5-trichloro-4-methylphenyl, 2,3,6- trichloro-4-methylphenyl, 3-bromo-4-methylphenyl, 2,5-dibromo-4-methylphenyl, 3,5-dibromo-4-methylphenyl, 2,3-difluoro-4-methylphenyl, 3-chloro-4-methoxyphenyl, 3-bromo-4-methoxyphenyl, 3,5-dibromo-4-methoxyphenyl, 2,3-difluoro-4-methoxyphenyl, 2,3-difluoro-4-ethoxyphenyl, 2,3-difluoro-4-propoxyphenyl and 4-ethenyl-2,3,5,6-tetrafluorophenyl.

Next, the examples of a case where $R^1$ in Formula (1) is substituted or unsubstituted arylalkyl shall be given. In alkylene of the arylalkyl, optional hydrogen may be replaced by fluorine, and optional —$CH_2$— may be replaced by —O—, —CH=CH— or cycloalkylene. The preferred example of the arylalkyl is phenylalkyl. In this case, the preferred carbon atom number of the alkylene is 1 to 12, and the more preferred carbon atom number is 1 to 8.

The examples of unsubstituted phenylalkyl are phenylmethyl, 2-phenylethyl, 3-phenylpropyl, 4-phenylbutyl, 5-phenylpentyl, 6-phenylhexyl, 11-phenylundecyl, 1-phenylethyl, 2-phenylpropyl, 1-methyl-2-phenylethyl, 1-phenylpropyl, 3-phenylbutyl, 1-methyl-3-phenylpropyl, 2-phenylbutyl, 2-methyl-2-phenylpropyl and 1-phenylhexyl.

In the phenylalkyl, optional hydrogen on a benzene ring may be replaced by halogen or alkyl having 1 to 12 carbon atoms. In this alkyl having 1 to 12 carbon atoms, optional hydrogen may be replaced by fluorine, and optional —$CH_2$— may be replaced by —O—, —CH=CH—, cycloalkylene or phenylene. The examples of phenylalkyl in which optional hydrogen on phenyl is replaced by fluorine are 4-fluorophenylmethyl, 2,3,4,5,6-pentafluorophenylmethyl, 2-(2,3,4,5,6-pentafluorophenyl)ethyl, 3-(2,3,4,5,6-pentafluorophenyl)propyl, 2-(2-fluorophenyl)propyl and 2-(4-fluorophenyl)propyl.

The examples of phenylalkyl in which optional hydrogen on a benzene ring is replaced by chlorine are 4-chlorophenylmethyl, 2-chlorophenylmethyl, 2,6-dichlorophenylmethyl, 2,4-dichlorophenylmethyl, 2,3,6-trichlorophenylmethyl, 2,4,6-trichlorophenylmethyl, 2,4,5-trichlorophenylmethyl, 2,3,4,6-tetrachlorophenylmethyl, 2,3,4,5,6-pentachlorophenylmethyl, 2-(2-chlorophenyl)ethyl, 2-(4-chlorophenyl)ethyl, 2-(2,4,5-chlorophenyl)ethyl, 2-(2,3,6-chlorophenyl)ethyl, 3-(3-chlorophenyl)propyl, 3-(4-chlorophenyl)propyl, 3-(2,4,5-trichlorophenyl)propyl, 3-(2,3,6-trichlorophenyl)propyl, 4-(2-chlorophenyl)butyl, 4-(3-chlorophenyl)butyl, 4-(4-chlorophenyl)butyl, 4-(2,3,6-trichlorophenyl)butyl, 4-(2,4,5-trichlorophenyl)butyl, 1-(3-chlorophenyl)ethyl, 1-(4-chlorophenyl)ethyl, 2-(4-chlorophenyl)propyl, 2-(2-chlorophenyl)propyl and 1-(4-chlorophenyl)butyl.

The examples of phenylalkyl in which optional hydrogen on phenyl is replaced by bromine are 2-bromophenylmethyl, 4-bromophenylmethyl, 2,4-dibromophenylmethyl, 2,4,6-tribromophenylmethyl, 2,3,4,5-tetrabromophenylmethyl, 2,3,4,5,6-pentabromophenylmethyl, 2-(4-bromophenyl)ethyl, 3-(4-bromophenyl)propyl, 3-(3-bromophenyl)propyl, 4-(4-bromophenyl)butyl, 1-(4-bromophenyl)ethyl, 2-(2-bromophenyl)propyl and 2-(4-bromophenyl)propyl.

The examples of phenylalkyl in which optional hydrogen on a benzene ring is replaced by alkyl having 1 to 12 carbon atoms are 2-methylphenylmethyl, 3-methylphenylmethyl, 4-methylphenylmethyl, 4-dodecylphenylmethyl, 3,5-dimethylphenylmethyl, 2-(4-methylphenyl)ethyl, 2-(3-methylphenyl)ethyl, 2-(2,5-dimethylphenyl)ethyl, 2-(4-ethylphenyl)ethyl, 2-(3-ethylphenyl)ethyl, 1-(4-methylphenyl)ethyl, 1-(3-methylphenyl)ethyl, 1-(2-methylphenyl)ethyl, 2-(4-methylphenyl)propyl, 2-(2-methylphenyl)propyl, 2-(4-ethylphenyl)propyl, 2-(2-ethylphenyl)propyl, 2-(2,3-dimethylphenyl)propyl, 2-(2,5-dimethylphenyl)propyl, 2-(3,5-dimethylphenyl)-propyl, 2-(2,4-dimethylphenyl)propyl, 2-(3,4-dimethylphenyl)propyl, 2-(3,5-dimethylphenyl)butyl, 4-(1-methylethyl)phenylmethyl, 2-(4-(1,1-dimethylethyl)phenyl)ethyl, 2-(4-(1-methylethyl)-phenyl)propyl and 2-(3-(1-methylethyl)phenyl)propyl.

The examples of phenylalkyl in which optional hydrogen on a benzene ring is replaced by alkyl having 1 to 12 carbon atoms and in which hydrogen in this alkyl is replaced by fluorine are 3-trifluoromethylphenylmethyl, 2-(4-trifluoromethylphenyl)ethyl, 2-(4-nonafluorobutyl-phenyl)ethyl, 2-(4-tridecafluorohexylphenyl)ethyl, 2-(4-heptadecafluorooctylphenyl)ethyl, 1-(3-trifluoromethylphenyl)ethyl, 1-(4-trifluoromethyl-phenyl)ethyl, 1-(4-nonafluorobutylphenyl)ethyl, 1-(4-tridecafluorohexylphenyl)ethyl, 1-(4-heptadecafluorooctylphenyl)ethyl, 2-(4-nonafluorobutylphenyl)propyl, 1-methyl-1-(4-nonafluorobutylphenyl)ethyl, 2-(4-tridecafluorohexylphenyl)propyl, 1-methyl-1-(4-tridecafluorohexyl-phenyl)ethyl, 2-(4-heptadecafluorooctylphenyl)propyl and 1-methyl-1-(4-heptadecafluorooctylphenyl)ethyl.

The examples of phenylalkyl in which optional hydrogen on a benzene ring is replaced by alkyl having 1 to 12 carbon atoms and in which —$CH_2$— in this alkyl is replaced by —CH=CH— are 2-(4-ethenylphenyl)ethyl, 1-(4-ethenylphenyl)ethyl and 1-(2-(2-propenyl)phenyl)ethyl.

The examples of phenylalkyl in which optional hydrogen on a benzene ring is replaced by alkyl having 1 to 12 carbon atoms and in which —$CH_2$— in this alkyl is replaced by —O— are 4-methoxyphenylmethyl, 3-methoxyphenylmethyl, 4-ethoxyphenylmethyl, 2-(4-methoxyphenyl)ethyl, 3-(4-methoxyphenyl)propyl, 3-(2-methoxyphenyl)propyl, 3-(3,4-dimethoxyphenyl)propyl, 11-(4-methoxyphenyl)undecyl, 1-(4-methoxyphenyl)ethyl, (3-methoxymethylphenyl)ethyl and 3-(2-nonadecafluorodecenyloxyphenyl)propyl.

The examples of phenylalkyl in which optional hydrogen on a benzene ring is replaced by alkyl having 1 to 12 carbon atoms and in which one of —$CH_2$— in this alkyl is replaced by cycloalkylene, to give the examples including a case in which another —$CH_2$— is replaced by —O—, are cyclopentylphenylmethyl, cyclopentyloxyphenylmethyl, cyclohexylphenylmethyl, cyclohexylphenylethyl, cyclohexylphenylpropyl and cyclohexyloxyphenylmethyl.

The examples of phenylalkyl in which optional hydrogen on a benzene ring is replaced by alkyl having 1 to 12 carbon atoms and in which one of —$CH_2$— in this alkyl is replaced by phenylene, to give the examples including a case in which another —$CH_2$— is replaced by —O—, are 2-(4-phenoxyphenyl)ethyl, 2-(4-phenoxyphenyl)propyl, 2-(2-phenoxyphenyl)propyl, 4-biphenylylmethyl, 3-biphenylylethyl, 4-biphenylylethyl, 4-biphenylylpropyl, 2-(2-biphenylyl)propyl and 2-(4-biphenylyl)propyl.

The examples of phenylalkyl in which at least two hydrogens on a benzene ring are replaced by different groups are 3-(2,5-dimethoxy-3,4,6-trimethylphenyl)propyl, 3-chloro-2-methylphenylmethyl, 4-chloro-2-methylphenylmethyl, 5-chloro-2-methylphenylmethyl, 6-chloro-2-methylphenylmethyl, 2-chloro-4-methylphenylmethyl, 3-chloro-4-methylphenylmethyl, 2,3-dichloro-4-methyl-phenylmethyl, 2,5-dichloro-4-methylphenylmethyl, 3,5-dichloro-4-methylphenylmethyl, 2,3,5-trichloro-4-methylphenylmethyl, 2,3,5,6-tetrachloro-4-methylphenylmethyl, 2,3,4,6-tetrachloro-5-methylphenylmethyl, 2,3,4,5-tetrachloro-6-methylphenylmethyl, 4-chloro-3,5-dimethylphenylmethyl, 2-chloro-3,5-dimethylphenylmethyl, 2,4-dichloro-3,5-dimethylphenylmethyl, 2,6-dichloro-3,5-dimethylphenylmethyl, 2,4,6-trichloro-3,5-dimethylphenylmethyl, 3-bromo-2-methylphenylmethyl, 4-bromo-2-methylphenylmethyl, 5-bromo-2-methylphenyl-methyl, 6-bromo-2-methylphenylmethyl, 3-bromo-4-methylphenylmethyl, 2,3-dibromo-4-methylphenylmethyl, 2,3,5-tribromo-4-methylphenylmethyl, 2,3,5,6-tetrabromo-4-methylphenylmethyl and 11-(3-chloro-4-methoxyphenyl)undecyl.

The most preferred examples of phenyl in the phenylalkyl are unsubstituted phenyl and phenyl having at least one of fluorine, alkyl having 1 to 4 carbon atoms, ethenyl and methoxy as a substituent. The examples of phenylalkyl in which —CH$_2$— in alkylene is replaced by —O—, —CH=CH— or cycloalkylene are 3-phenoxypropyl, 1-phenylethenyl, 2-phenylethenyl, 3-phenyl-2-propenyl, 4-phenyl-4-pentenyl, 13-phenyl-12-tridecenyl, phenylcyclohexyl and phenoxycyclohexyl. The examples of phenylalkenyl in which hydrogen on a benzene ring is replaced by fluorine or methyl are 4-fluorophenylethenyl, 2,3-difluorophenylethenyl, 2,3,4,5,6-pentafluorophenylethenyl and 4-methylphenylethenyl.

Among the above groups, the preferred examples of R$^1$ are groups selected from alkyl having 1 to 8 carbon atoms, substituted or unsubstituted phenyl, substituted or unsubstituted phenylalkyl and naphthyl. The more preferred examples of R$^1$ are groups selected from substituted or unsubstituted phenyl, substituted or unsubstituted phenylalkyl and naphthyl. In this case, in the alkyl having 1 to 8 carbon atoms, optional hydrogen may be replaced by fluorine, and optional —CH$_2$— may be replaced by —O—, —CH=CH—, cycloalkylene or cycloalkenylene. In the substituted or unsubstituted phenyl, optional hydrogen may be replaced by halogen, methyl or methoxy.

In the substituted or unsubstituted phenylalkyl, the alkylene has 1 to 8 carbon atoms; optional hydrogen on a benzene ring may be replaced by fluorine, alkyl having 1 to 4 carbon atoms, vinyl or methoxy; and optional —CH$_2$— in the alkylene may be replaced by —O—, —CH=CH— or cycloalkylene. In the above groups, when the phenyl has plural substituents, these substituents may be the same group or different groups. All of R$^1$ in Formula (1) are preferably the same group selected from the above preferred examples.

The more preferred specific examples of R$^1$ are phenyl, halogenated phenyl, phenyl having at least one methyl, methoxyphenyl, naphthyl, phenylmethyl, phenylethyl, phenylbutyl, 2-phenylpropyl, 1-methyl-2-phenylethyl, pentafluorophenylpropyl, 4-ethylphenylethyl, 3-ethylphenylethyl, 4-(1,1-dimethylethyl)phenylethyl, 4-ethenylphenylethyl, 1-(4-ethenylphenyl)ethyl, 4-methoxyphenylpropyl and phenoxypropyl. Among the above examples, phenyl is most preferred.

Next, a production process for the compound (2) shall be explained. The compound (2) can readily be produced at a good yield by hydrolyzing a compound (7) in an organic solvent containing an oxygen atom in a molecule under the presence of monovalent alkaline metal hydroxide and then subjecting it to polycondensation:

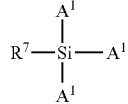

(7)

In Formula (7), R$^7$ is defined in the same manner as R$^2$ in Formula (2), and A$^1$ is a hydrolytic group. Accordingly, the most preferred examples of R$^7$ are, as described above, phenyl, halogenated phenyl, phenyl having at least one methyl, methoxyphenyl, naphthyl, phenylmethyl, phenylethyl, phenylbutyl, 2-phenylpropyl, 1-methyl-2-phenylethyl, pentafluorophenylpropyl, 4-ethylphenylethyl, 3-ethylphenylethyl, 4-(1,1-dimethylethyl)phenylethyl, 4-ethenylphenylethyl, 1-(4-ethenylphenyl)ethyl, 4-methoxyphenylpropyl and phenoxypropyl. The preferred examples of A$^1$ are chlorine, acetoxy and alkoxy. This alkoxy group is a group eliminated by hydrolysis, and therefore it is not so meaningful to restrict the range of the number of the carbon atom thereof. However, considering the availability thereof, the number of the carbon atom thereof is 1 to 4.

The examples of the compound (7) are phenyltrichlorosilane, phenyltrimethoxysilane, phenyltriethoxysilane, phenyltri-n-propoxysilane, phenyltriisopropoxysilane, phenyltri-n-butoxysilane, p-tolyltrimethoxysilane, p-tolyltriethoxysilane, chlorophenyltrichlorosilane, chlorophenyltrimethoxysilane and chlorophenyltriethoxysilane.

A large part of the compounds (7) described above is commercially available. However, the compounds which are not commercially available can be obtained by publicly known synthetic techniques, for example, by a method in which halosilane is reacted with a Grignard reagent.

Next, the monovalent alkaline metal hydroxide used for producing the compound (2) shall be explained. Lithium hydroxide, sodium hydroxide, potassium hydroxide and cesium hydroxide can be given as the examples of the monovalent alkaline metal hydroxide, and considering the availability thereof, sodium hydroxide and potassium hydroxide are preferred.

An addition amount of the monovalent alkaline metal hydroxide in producing the compound (2) is 0.3 to 1.5, more preferably 0.4 to 0.8 in terms of a molar ratio to the compound (7). If the molar ratio falls in the above range, cyclic or linear low molecular weight siloxane compounds and high molecular weight siloxane compounds are prevented from being formed, and the compound (2) can readily be obtained.

Next, an addition amount of water shall be explained. An addition amount of water is 1.0 to 1.5, more preferably 1.1 to 1.3 in terms of a molar ratio to the compound (7). If it falls in the above range, remaining of the hydrolytic group, formation of low molecular weight siloxane compounds and formation of high molecular weight siloxane compounds can be prevented. Addition timing of water shall not specifically be restricted, and it may be mixed in advance with other raw materials or may be added later.

Further, hydrolytic reaction of the compound (7) is carried out preferably under the presence of an organic solvent containing an oxygen atom in a molecule. The preferred examples of the above organic solvent are linear, branched or cyclic monohydric alcohols. The examples of the linear alcohols are methanol, ethanol, 1-propanol, 1-butanol, 1-pentanol, 1-hexanol, 1-heptanol and 1-octanol. The examples of the branched alcohols are 2-propanol, 2-butanol, 2-methyl-2-propanol, 2-hexanol and 3-hexanol. The examples of the cyclic alcohols are cyclopentanol, cyclohexanol and cycloheptanol.

As described above, the organic solvent is preferably used in producing the compound (2), and the above organic solvents may be used alone or plural organic solvents may be used in a mixture. A use amount thereof shall not specifically be restricted. Factors for determining a use amount of the organic solvent are economical viewpoints such as energy efficiency and a time efficiency and a stirring efficiency. Accordingly, the use amount range which has to be strictly kept is not present, and considering the factors described above, it shall be 0.3 to 50 times, more preferably 5 to 40 times in terms of a volume ratio to the compound (7). It is important to adopt the optimum conditions in the range of the production conditions described above according to the compound (7) used as the raw material.

The compound (2) is scarcely soluble in organic solvents, and therefore it starts to be deposited as the reaction goes on. Time required for deposition is varied according to the conditions such as the organic solvent used and a use amount thereof, and it is usually several minutes to several ten hours. The compound (2) deposited can readily be separated from the organic solvent by filtering.

However, the compound (2) obtained has a low solubility in organic solvents, and therefore an analytical method for analyzing the structure thereof is restricted. Accordingly, if capping reaction is carried out by trimethylchlorosilane to raise the solubility thereof in organic solvents, it shall become possible to readily carry out the structural analysis thereof.

If at least two compounds (7) are used in synthesizing the compound (2), the compound (2) in which eight $R^2$ in Formula (2) are constituted of at least two different groups can be obtained.

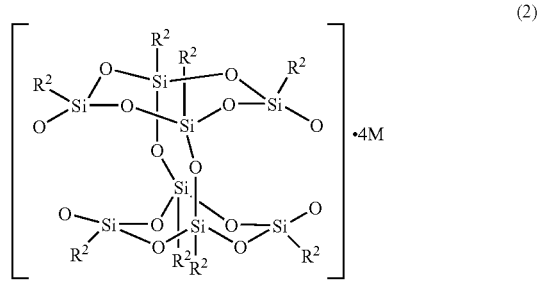

(2)

In Formula (2), $R^2$ is defined in the same manner as $R^1$ in Formula (1), and M is a monovalent alkaline metal atom.

Next, a production process for the compound (1) shall be explained. The compound (1) can be obtained by mixing the compound (2) obtained by the method described above, if necessary, with an organic solvent and adding a proton donor to this mixture to react them.

The organic solvent used for the above reaction shall not specifically be restricted as long as it does not hinder the progress of the reaction. It includes, for example, aliphatic hydrocarbons such as hexane and heptane, aromatic hydrocarbons such as benzene, toluene and xylene, ethers such as diethyl ether, tetrahydrofuran and dioxane, halogenated hydrocarbons such as methylene chloride and carbon tetrachloride and acetates such as methyl acetate, ethyl acetate and butyl acetate, and tetrahydrofuran and acetates are preferred.

A preferred proportion of the compound (2) mixed with the organic solvent falls in a range of 0.05 to 50% by weight based on the weight of the solvent. If it is 50% by weight or less, a concentration of the by-produced salts can be reduced, and it is advantageous for allowing the reaction to proceed. On the other hand, if it is 0.05% by weight or more, it is preferred in terms of the cost. The more preferred proportion falls in a range of 1 to 10% by weight.

Next, the proton donor used for the above reaction shall be explained. The proton donor is a Brønsted acid (hereinafter referred to as the acid). The above proton donor may be an inorganic acid or an organic acid and shall not specifically be restricted as long as it reacts with the compound (2) to form the compound (1). Capable of being specifically given as the examples thereof are, for example, cyanic acid, isocyanic acid, thiocyanic acid, isothiocyanic acid, nitric acid, nitrous acid, sulfuric acid, sulfurous acid, carbonic acid, hydrochloric acid, hydrobromic acid, phosphoric acid, boric acid, formic acid, acetic acid, propionic acid, butyric acid, stearic acid, oxalic acid, malonic acid, succinic acid, adipic acid, acrylic acid, methacrylic acid, oleic acid, maleic acid, chloroformic acid, chloroacetic acid, trifluoroacetic acid, cyclohexanecarboxylic acid, pivalic acid, benzoic acid, toluic acid, naphthoic acid, phthalic acid, cinnamic acid, nicotinic acid, thiophenecarboxylic acid, S-thioacetic acid, dithioacetic acid, S-thiobenzoic acid, dithiobenzoic acid, thiocarbonic acid, trithiocarbonic acid, xanthic acid, methanesulfonic acid, benzenesulfonic acid, p-toluenesulfonic acid, phenylphosphonic acid and diphenylphosphinic acid. Considering handling, hydrochloric acid, nitric acid, sulfuric acid, p-toluenesulfonic acid and carboxylic acids are preferred, and hydrochloric acid and acetic acid are more preferred.

An addition amount of the above acids is varied depending on the kind of the acid added, and it falls in a range of preferably 4 times mole or more and 40 times mole or less, more preferably 4 times mole or more and 10 times mole or less based on the compound (2). If they are added in 4 times mole or more, the compound (2) can completely be converted to the silanol. If the reaction is carried out in 4 times mole or less, an Si—ONa bond is likely to partially remain. On the other hand, if the acid is added too much, the resulting silanol falls in an instable state and is likely to be condensed.

A temperature of this reaction falls, though depending on the kind of the compound (2), in a range of preferably −80 to 150° C., more preferably 0 to 70° C. in order to sufficiently complete the reaction. If the reaction is carried out at a high temperature exceeding 150° C., the resulting silanol falls in an instable state and is likely to be condensed. The reaction time is 0.1 to 8 hours, though this range of the reaction time shall not restrict the present invention since the reaction time is influenced by a concentration of the reaction solution, the reaction temperature and stirring in addition to a reactivity of the compound (2).

As described above, the compound (1) can stably be obtained from the compound (2) by carrying out the reaction, and if the product having a higher purity is required, the object thereof can be achieved by carrying out recrystallization, extraction and washing.

Next, a production process for polysiloxane using the compound (1) shall be explained. The compound (1) has active silanol, and therefore various polysiloxanes can be obtained by reacting it with organosilicon compounds having a hydrolytic group or silanol. For example, when polysiloxane is obtained only from the compound (1), the compound (1) is dissolved, if necessary, in a solvent, and a condensation catalyst is added, if necessary, to carry out polycondensation reaction, whereby polysiloxane represented by Formula (3) can be obtained.

The reaction can be allowed to effectively proceed to obtain polysiloxane by adding a condensation catalyst in the reaction and carrying out the reaction while drawing out water to the outside of the system.

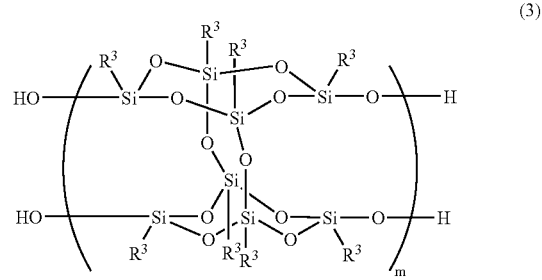

(3)

In Formula (3), $R^3$ is a group defined in the same manner as $R^1$ in Formula (1) of the item [1], and m is an integer of 2 to 1000.

In the present invention, silsesquioxane, silicone and silicon resins each having an alkoxysilyl group, an acetoxysilyl group, an aminosilyl group or a halosilyl group can be given as the examples of the organosilicon compound having a hydrolytic group. To be specific, a compound having an incompletely condensed type structure represented by Formula (4) and a cyclic organosilicon compound represented by Formula (5) can be given as the examples of the organosilicon compound having silanol. Among the organosilicon compounds represented by Formula (4), the compounds in which a substituent represented by $R^4$ is ethyl, isobutyl, cyclopentyl, cyclohexyl or isooctyl are commercially available and can readily be obtained. The compounds which are not commercially available can be obtained as well by the methods shown in the non-patent documents 2 to 5 and the patent document 1.

The cyclic silsesquioxane represented by Formula (5) can be obtained by subjecting trichlorosilane or trialkoxysilane to hydrolysis and polycondensation by the publicly known technique shown in the non-patent document 2, 4 or 6.

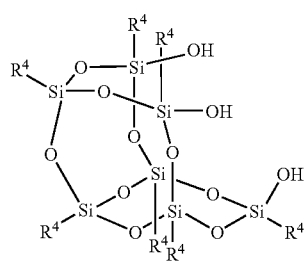

(4)

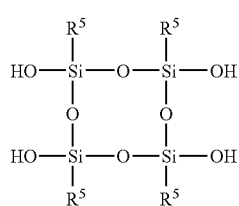

(5)

In Formula (4) and Formula (5), $R^4$ and $R^5$ are groups defined in the same manner as $R^1$ in Formula (1).

Further, silicone represented by Formula (8) can also be used as the organosilicon compound having a hydrolytic group.

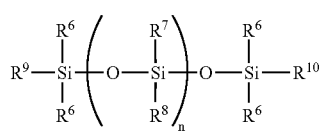

(8)

In Formula (8), $R^6$ to $R^8$ have the same meaning as that of $R^1$ in Formula (1), and $R^9$ and $R^{10}$ are a hydroxyl group, a hydrolytic group or a group defined in the same manner as $R^1$ in Formula (1). However, $R^9$ and $R^{10}$ are not the group defined in the same manner as $R^1$ in Formula (1) at the same time, and n is an integer of 2 to 500.

To be specific, capable of being given as the examples of the silicone having a hydroxyl group are DMS-S12 (product name, manufactured by AZmax Co., Ltd.), DMS-S15 (product name, manufactured by AZmax Co., Ltd.), DMS-S21 (product name, manufactured by AZmax Co., Ltd.), DMS-S27 (product name, manufactured by AZmax Co., Ltd.), DMS-S31 (product name, manufactured by AZmax Co., Ltd.), DMS-S32 (product name, manufactured by AZmax Co., Ltd.), DMS-S33 (product name, manufactured by AZmax Co., Ltd.), DMS-S35 (product name, manufactured by AZmax Co., Ltd.), DMS-S38 (product name, manufactured by AZmax Co., Ltd.), DMS-S42 (product name, manufactured by AZmax Co., Ltd.), DMS-S45 (product name, manufactured by AZmax Co., Ltd.), DMS-S51 (product name, manufactured by AZmax Co., Ltd.), PSD-0332 (product name, manufactured by AZmax Co., Ltd.), PDS-1615 (product name, manufactured by AZmax Co., Ltd.), PDS-9931 (product name, manufactured by AZmax Co., Ltd.) and FMS-9921 (product name, manufactured by AZmax Co., Ltd.).

DMS-X11 (product name, manufactured by AZmax Co., Ltd.) and DMS-X25 (product name, manufactured by AZmax Co., Ltd.) can be given as the examples of silicone having an alkoxysilyl group as a hydrolytic group. Capable of being given as the examples of silicone having a chlorosilyl group as a hydrolytic group are DMS-K05 (product name, manufactured by AZmax Co., Ltd.), DMS-K13 (product name, manufactured by AZmax Co., Ltd.) and DMS-K26 (product name, manufactured by AZmax Co., Ltd.). DMS-D33 (product name, manufactured by AZmax Co., Ltd.) can be given as the example of silicone having an acetoxysilyl group as a hydrolytic group. DMS-N05 (product name, manufactured by AZmax Co., Ltd.) can be given as the example of silicone having an aminosilyl group as a hydrolytic group. All the above compounds are commercially available from AZmax Co., Ltd. and can easily be obtained.

Also, the compounds having a hydroxyl group at one end which are not commercially available can be obtained as well by a method disclosed in the patent document 2 by Nakano et al., that is, by subjecting cyclic polysiloxane to anionic polymerization using triorganosilanol as an initiator under the presence of 0.12 to 2.0 mole % of a lithium base catalyst. Further, the compounds having hydroxyl groups at both ends can be obtained by a method disclosed in the patent document 3 by Akutsu et al., that is, by subjecting cyclic polysiloxane to anionic polymerization in a polar solvent having no active hydrogen using water as an initiator under the presence of 0.12 to 10 mole % of a lithium base catalyst based on the initiator.

In producing the polysiloxane of the present invention, a solvent is not necessarily required, but it can be used in the present invention as long as it does not hinder the progress of the reaction. Capable of being specifically given as the examples thereof are, for example, aromatic hydrocarbons such as benzene, toluene and xylene, aliphatic hydrocarbons such hexane and heptane, alcohols such as methanol, ethanol, n-propanol and iso-propanol, ethers such as dimethyl ether, diethyl ether, tetrahydrofuran and 1,4-dioxane, acetates such as methyl acetate, ethyl acetate and butyl acetate, amides such as N,N-dimethylformamide, N,N-dimethylacetamide and N-methyl-2-pyrrolidone, ketones such as acetone, 2-butanone and methyl iso-butyl ketone, acetonitrile and dimethylsulfoxide. Among them, tetrahydrofuran, acetates, dimethylformamide and toluene are preferred. In the present invention, an addition amount thereof shall not be restricted, and it is 0.01 to 100 parts by weight per one part by weight of the compound (1).

Usually known polycondensation catalysts for silanol can be used as the polycondensation catalyst used in the present invention. Capable of being given as the examples thereof are, for example, alkaline compounds such as sodium hydroxide and potassium hydroxide, amines such as ethylenediamine, N,N,N',N'-tetramethylethylenediamine, diethylenetriamine, triethylamine, tributylamine, dimethylaniline, 1,4-diazabicyclo[2.2.2]octane, 1,8-diazabicyclo[5.4.0]undeca-7-ene and 2,5-diazabicyclo[2.2.1]heptane, quaternary ammonium salts such as tetramethylammonium acetate, tetramethylammonium hydroxide and ammonium perchrorate, carbodiimides such as dicyclohexylcarbodiimide and 1-ethyl-3-(3-dimethylaminopropyl)carbodiimide, organic titanium compounds such as tetraisopropyl titanate, tetra-n-butyl titanate, titanium diacetylacetonate and titanium diisopropyl-bisacetylacetonate, organic tin compounds such as dibutyltin diacetate, dibutyltin dioctate, dibutyltin dilaurate and dibutyltin maleate, acid compounds such as hydrochloric acid, trichloroacetic acid, p-toluenesulfonic acid, phosphoric acid, acetic acid and acetic anhydride, a reaction product of n-hexylamine and 2-ethylhexanoic acid and a reaction product of tetramethylguanidine and 2-ethylhexanoic acid. An addition amount of the above polycondensation catalysts falls, though varied depending on the kind thereof, in a range of usually 0.01 to 100 parts by weight per 100 parts by weight of the compound (1).

The polysiloxane thus obtained which is soluble in a solvent makes it possible to provide a flat, even and transparent thin film by spin coating in the form of a solution. Accordingly, it is useful as an electronic material, an optical material, a coating material and a sealing material, and it is expected to be applied to them.

EXAMPLES

The present invention shall be explained below in details with reference to examples, but the present invention shall not be restricted by these examples. In chemical formulas in the following examples, Ph represents phenyl; Me represents methyl; and TMS represents trimethylsilyl. The average molecular weight is a value measured by gel permeation chromatography (GPC) using tetrahydrofuran as a solvent and calculated from a calibration curve prepared using standard polystyrene. The nuclear magnetic resonance spectrum was measured using tetramethylsilane as an internal standard substance.

Example 1

<Synthesis of Organosilicon Compound>

A reactor of 50 liter equipped with a reflux condenser, a thermometer and a stirrer was charged with phenyltrimethoxysilane (6.54 kg), 2-propanol (26.3 liter), purified water (0.66 kg) and sodium hydroxide (0.88 kg) and sealed with nitrogen. The reactor was heated while heating to carry out reaction for 5 hours in a refluxing state. After finishing the reaction, the reactor was left standing at room temperature for 15 hours, and then the supernatant was removed by decantation. 2-Propanol (9.87 kg) was added thereto and stirred, and then the solution was filtrated by means of a pressure filter equipped with a filter paper (No. 2) manufactured by Advantech Co., Ltd. to obtain a white solid matter. Then, the white solid matter obtained was transferred into a vat made of stainless steal which was lined with a polytetrafluoroethylene sheet, and it was dried at an inside temperature of 80° C. and a pressure of 6.7×10⁻⁴ MPa for 24 hours by means of a vacuum dryer to obtain 2.22 kg of a white solid matter of a powder form.

<Confirmation of the Structure of the White Solid Matter of a Powder Form>

A reaction vessel having a content volume of 50 ml equipped with a dropping funnel and a thermometer was charged with the white solid matter of a powder form (1.2 g) obtained above, THF (15 g) and triethylamine (1.4 g), and the vessel was sealed with dry nitrogen. Chlorotrimethylsilane (2.5 g) was dropwise added thereto from the dropping funnel under stirring by means of a magnetic stirrer. After continuing to stir the solution at 25° C. for 4 hours, ion-exchanged water (10 g) was added thereto and stirred for 5 minutes, and then toluene (15 g) was added and stirred for 10 minutes. The reaction mixture thus obtained was separated into an organic layer and an aqueous layer, and the organic layer was repeatedly washed with ion-exchanged water to confirm that the washing solution was neutral. The organic layer was dried on anhydrous magnesium sulfate and concentrated under reduced pressure to obtain 1.2 g of a white solid matter. The white solid matter thus obtained was analyzed by means of GPC, $^1$H-NMR and $^{29}$Si-NMR to carry out structural analysis. The results thereof are shown below.

GPC:
  Number average molecular weight (Mn)=950
  Weight average molecular weight (Mw)=990
$^1$H-NMR (CDCl$_3$):
  δ (ppm)=0.05[s, 36H, —Si(CH$_3$)$_3$], 7.09 to 7.50[m, 40H, —SiC$_6$H$_5$]
$^{29}$Si-NMR (CDCl$_3$):
  δ (ppm)=-78.95, -76.12[s, 1:1, —SiC$_6$H$_5$], 10.62[s, —Si(CH$_3$)$_3$]

The analytical results described above supported a structure of Formula (a). Accordingly, it is judged that the compound before trimethylsilylated has a chemical structure represented by Formula (9).

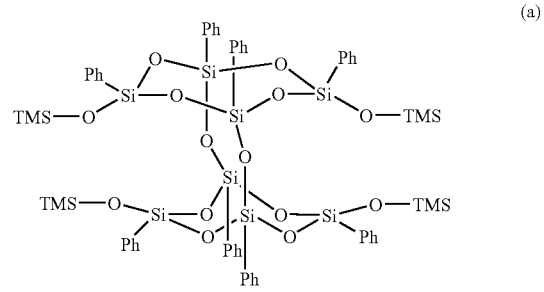

(a)

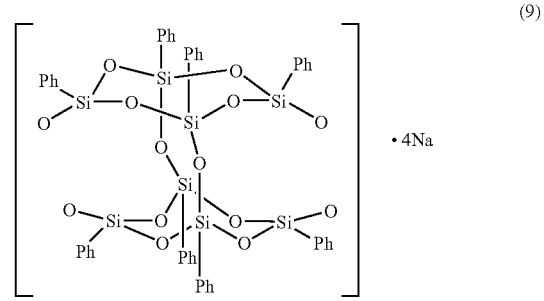

(9)

Example 2

<Synthesis of Organosilicon Compound Having Silanol>

A reaction vessel of 200 ml equipped with a dropping funnel, a thermometer and a rotator was charged with the organosilicon compound (9) (10 g) obtained in Example 1 and butyl acetate (100 ml), and the vessel was sealed with nitrogen and cooled on an ice bath. Acetic acid (3.0 g) was dropwise added under stirring by means of a magnetic stirrer while maintaining the solution temperature at 10° C. or lower.

After finishing dropwise adding, stirring was continued at 0° C. for 2 hours, and then ion-exchanged water (20 g) was dropwise added. After finishing dropwise adding, stirring was continued for 10 minutes, and then the solution was transferred into a separating funnel and separated into an organic layer and an aqueous layer. The organic layer thus obtained was neutralized by a saturated sodium hydrogencarbonate aqueous solution, and then it was washed twice with saturated brine and twice with ion-exchanged water. The organic layer was dried on anhydrous magnesium sulfate, filtered and then concentrated (oil bath temperature: 45° C.) under vacuum by means of a rotary evaporator. Next, acetone (24.0 g) was added to the resulting residue, and the mixture was stirred at room temperature for 10 minutes. Then, the solution was filtrated under reduced pressure through a membrane filter having a pore diameter of 3 μm to obtain a white solid matter. The white solid matter thus obtained was dried at room temperature under vacuum to result in obtaining 10.0 g of a white solid matter of a powder form.

The white solid matter of a powder form thus obtained was subjected to structural analysis by means of an infrared absorption spectrum (IR), $^{29}$Si-NMR and GPC. The results thereof are shown below.

IR (KBr):
  $\nu(nu)=3300cm^{-1}$[Si-OH]$950cm^{-1}$[Si-OH]
$^{29}$Si-NMR(THF):
  δ (ppm)=−69.32[s, -PhSi(OH)O$_{2/2}$], −79.45[s, -PhSiO$_{3/2}$]
GPC:
  Number average molecular weight (Mn)=760
  Weight average molecular weight (Mw)=780

The data described above indicated that the white solid matter of a powder form has a structure of Formula (10).

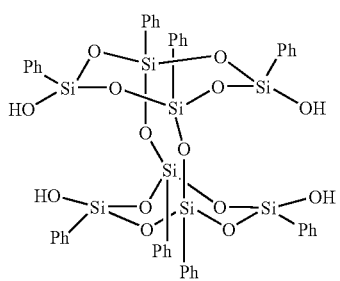

(10)

Example 3

<Synthesis of Organosilicon Compound Having Silanol>

A reaction vessel having a volume content of 100 ml equipped with a dropping funnel and a thermometer was charged with the organosilicon compound (9) (6 g) obtained in Example 1 and tetrahydrofuran (50 ml), and the vessel was sealed with dry nitrogen. Then, acetic acid (2.4 g) was dropwise added in about 10 seconds under stirring while maintaining the solution temperature at 22 to 27° C. After finishing dropwise adding, stirring was continued at room temperature for one hour, and then ion-exchanged water (20 g) was dropwise added thereto. After finishing dropwise adding, stirring was continued for 10 minutes, and then the solution was transferred into a separating funnel to separate an organic layer from an aqueous layer. The organic layer thus obtained was washed once with a saturated sodium hydrogencarbonate aqueous solution, and then it was repeatedly washed with water to confirm that the washing solution was neutral. Next, the organic layer was dried on anhydrous magnesium sulfate and then concentrated under vacuum to obtain 5.3 g of a white solid matter of a powder form.

The white solid matter of a powder form thus obtained was analyzed in the same manner as in Example 2. As a result thereof, the same spectra as in Example 2 were obtained, and it was confirmed that the above white solid matter of a powder form had the same structure as that of Formula (10).

Example 4

<Synthesis of Polysiloxane>

A reaction vessel of 200 ml equipped with a reflux condenser and a rotator was charged with the organosilicon compound (10) (5 g) obtained in Example 2 and toluene (120 ml). A molar ratio 1:2 mixed solution of n-hexylamine/2-ethylhexanoic acid (0.05 g) was added thereto, and the vessel was sealed with nitrogen. Then, the vessel was heated on an oil bath while stirring by means of a magnetic stirrer. After the reaction solution reached a refluxing state, the reaction was continued for 16.5 hours. Thereafter, the solution was cooled down to room temperature and filtered, and then it was concentrated under reduced pressure to obtain a white solid matter.

The white solid matter thus obtained was analyzed by GPC to find that the number average molecular weight (Mn) was 1500 and that the weight average molecular weight (Mw) was 3300. As a result thereof, it was confirmed that the white solid matter thus obtained was a polycondensation product of the organosilicon compound (10).

Example 5

<Synthesis of Polysiloxane>

A reaction vessel of 100 ml equipped with a reflux condenser and a rotator was charged with the organosilicon compound (10) (2.14 g) obtained in Example 2, dimethylsulfoxide (30 ml) and N,N-dicyclohexylcarbodiimide (1.24 g) and sealed with nitrogen. Then, the vessel was heated on an oil bath while stirring by means of a magnetic stirrer. After the reaction solution reached 125° C., the reaction was continued for 43 hours and, then the solution was cooled down to room temperature. The solution was repeatedly washed three times with water, dried on anhydrous magnesium sulfate and filtered, and then it was concentrated under reduced pressure to obtain 0.6 g of a white solid matter.

The white solid matter thus obtained was measured for a molecular weight by GPC to find that the number average molecular weight (Mn) was 3000 and that the weight average molecular weight (Mw) was 3800. As a result thereof, it was confirmed that the white solid matter thus obtained was a polycondensation product of the organosilicon compound (10).

Example 6

<Synthesis of Polysiloxane>

A reaction vessel of 200 ml equipped with a reflux condenser, a rotator and a deanstark filled with molecular sieve 3A is charged with the organosilicon compound (10) (5 g) obtained in Example 2 and toluene (120 ml). p-Toluenesulfonic acid monohydrate (0.05 g) is added thereto, and the vessel is sealed with nitrogen. Then, the vessel is heated on an oil bath while stirring by means of a magnetic stirrer. After the reaction solution reach a refluxing state, the reaction is continued for 24 hours. Thereafter, the solution is cooled down to room temperature and washed once with a saturated sodium hydrogencarbonate aqueous solution, and then it is washed three times with ion-exchanged water to confirm that the washing solution is neutral. The organic layer obtained is dried on anhydrous magnesium sulfate, and then it is filtered and concentrated under vacuum to obtain a white solid matter.

The above white solid matter is measured for a molecular weight by GPC to find that the number average molecular weight (Mn) is 30000 and that the weight average molecular weight (Mw) is 100000 and, it is confirmed that the above white solid matter is a polycondensation product of the organosilicon compound (10).

Example 7

<Synthesis of Polysiloxane>

A reaction vessel of 50 ml equipped with a reflux condenser, a rotator and a thermometer was charged with the organosilicon compound (10) (1.00 g) obtained in Example 2, dimethylsiloxane having chlorine at both ends as silicone having a hydrolytic group, DMS-K05 (0.85 g) manufactured by AZmax Co., Ltd. and tetrahydrofuran (20 g), and the vessel was sealed with nitrogen. Reaction was carried out at room temperature for 1.5 hour while stirring by means of a magnetic stirrer, and then triethylamine (0.40 g) was charged thereinto. Then, the vessel was heated on an oil bath to carry out refluxing for 5 hours. The solution was cooled down to room temperature and then washed once with 1N hydrochloric acid and three times with ion-exchanged water. The organic layer was dried on anhydrous magnesium sulfate, filtered and then concentrated under vacuum to obtain 0.6 g of a viscous liquid.

The viscous liquid thus obtained was measured for a molecular weight by GPC to find that the number average molecular weight (Mn) was 3000 and that the weight average molecular weight (Mw) was 3800. As a result thereof, it was confirmed that the viscous liquid obtained was polysiloxane comprising the organosilicon compound (10) and dimethylsilicone.

What is claimed is:

1. Polysiloxane represented by Formula (3):

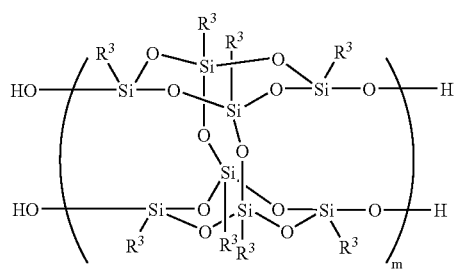

(3)

wherein $R^3$ is a group selected independently from hydrogen, alkyl having 1 to 45 carbon atoms, substituted or unsubstituted aryl, and arylalkyl; in which in the alkyl optional hydrogen may be replaced by fluorine and optional —$CH_2$— may be replaced by —O—, —CH=CH—, cycloalkylene, or cycloalkenylene, and arylalkyl is constituted of alkylene in which optional hydrogen may be replaced by fluorine and optional —$CH_2$— may be replaced by —O—, —CH=CH— or cycloalkylene, and substituted or unsubstituted aryl, and m is an integer of 2 to 1000.

2. The polysiloxane according to claim 1, wherein m is an integer of 2 to 500.

3. The polysiloxane according to claim 1, wherein m is an integer of 2 to 50.

4. Polysiloxane obtained by subjecting only an organosilicon compound represented by Formula (1) to polycondensation reaction:

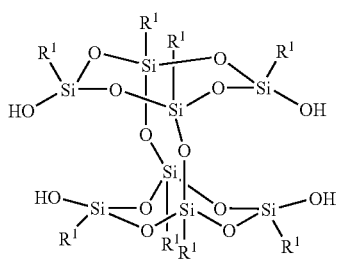

(1)

wherein each $R^1$ is a group selected independently from hydrogen, alkyl having 1 to 45 carbon atoms, substituted or unsubstituted aryl, and arylalkyl; in which in the alkyl optional hydrogen may be replaced by fluorine and optional —$CH_2$— may be replaced by —O—, —CH=CH—, cycloalkylene, or cycloalkenylene, and arylalkyl is constituted of alkylene in which optional hydrogen may be replaced by fluorine and optional —$CH_2$— may be replaced by —O—, —CH=CH— or cycloalkylene, and substituted or unsubstituted aryl.

5. Polysiloxane obtained by reacting the organosilicon compound according to claim 4 with an organosilicon compound represented by Formula (8) having hydrolytic group

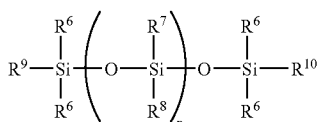

(8)

wherein $R^6$ to $R^8$ have the same meaning as that of $R^1$ in Formula (1), $R^9$ and $R^{10}$ are a hydroxyl group or a hydrolytic group, and n is an integer of 2 to 500.

6. Polysiloxane obtained by reacting the organosilicon compound according to claim 4 with an organosilicon compound represented by Formula (4), (5) or (8) having silanol

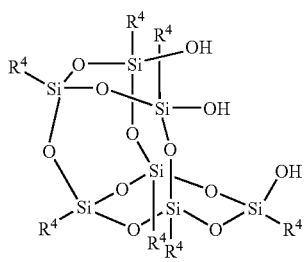

(4)

-continued

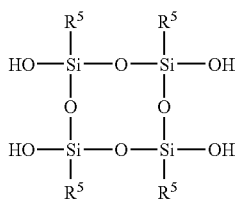
(5)

wherein, in Formula (4) and Formula (5), $R^4$ and $R^5$ are groups defined in the same manner as $R^1$ in Formula (1),

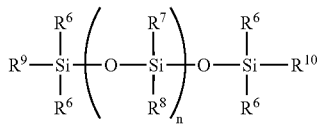
(8)

wherein $R^6$ to $R^8$ have the same meaning as that of $R^1$ in Formula (1), $R^9$ and $R^{10}$ are a hydroxyl group or a hydrolytic group, and n is an integer of 2 to 500.

7. The polysiloxane according to claim 5, wherein the hydrolytic groups are alkoxysilyl groups.

8. The polysiloxane according to claim 5, wherein the hydrolytic groups are acetoxysilyl groups.

9. The polysiloxane according to claim 5, wherein the hydrolytic groups are halosilyl groups.

10. The polysiloxane according to claim 5, wherein the hydrolytic groups are aminosilyl groups.

11. A production process for polysiloxane consisting of subjecting only an organosilicon compound represented by Formula (1)

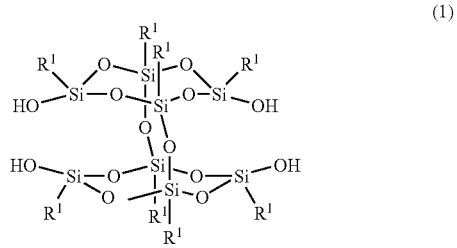
(1)

wherein each $R^1$ is a group selected independently from hydrogen, alkyl having 1 to 45 carbon atoms, substituted or unsubstituted aryl, and arylalkyl; in which in the alkyl optional hydrogen may be replaced by fluorine and optional —$CH_2$— may be replaced by —O—, —CH=CH—, cycloalkylene, or cycloalkenylene, and arylalkyl is constituted of alkylene in which optional hydrogen may be replaced by fluorine and optional —$CH_2$— may be replaced by —O—, —CH=CH— or cycloalkylene, and substituted or unsubstituted aryl to polycondensation reaction.

* * * * *